(12) United States Patent
Raphael (10) Patent No.: US 8,123,706 B2
(45) Date of Patent: Feb. 28, 2012

(54) FREQUENCY-BASED METHODS, SYSTEM AND APPARATUS FOR CAVITY RECONSTRUCTION VIA AREA-DISTANCE PROFILES

(75) Inventor: David T. Raphael, Valley Village, CA (US)

(73) Assignee: University of Southern California, Los Angeles, CA (US)

( * ) Notice: Subject to any disclaimer, the term of this patent is extended or adjusted under 35 U.S.C. 154(b) by 1022 days.

(21) Appl. No.: 11/688,192

(22) Filed: Mar. 19, 2007

(65) Prior Publication Data
US 2007/0286024 A1 Dec. 13, 2007

Related U.S. Application Data (60) Provisional application No. 60/783,740, filed on Mar. 17, 2006.

(51) Int. Cl.
*A61B 7/00* (2006.01)
*A61B 5/103* (2006.01)
*A61B 5/117* (2006.01)

(52) U.S. Cl. .......... 600/593; 600/586; 600/587
(58) Field of Classification Search .......... 600/586, 600/587, 593
See application file for complete search history.

(56) References Cited

U.S. PATENT DOCUMENTS 4,265,235 A 5/1981 Fukunaga
(Continued)

OTHER PUBLICATIONS

Forbes et al., "Singular system methods in acoustic pulse reflectometry" ACTA Acustica United with Acustica, vol. 89, No. 5, pp. 743-753, Sep. 2003.

(Continued)

*Primary Examiner* — Max Hindenburg
*Assistant Examiner* — Sean Dougherty
(74) *Attorney, Agent, or Firm* — DLA Piper LLP (US)

(57) ABSTRACT

A method, system and apparatus for Resonance-Based Acoustic Reflectometry that uses a hybrid approach. A method of manufacture, system and apparatus for a modified circle system that allows for the connection of extra devices like exemplary embodiments of the present invention.

12 Claims, 7 Drawing Sheets

U.S. PATENT DOCUMENTS

| | | |
|---|---|---|
| 5,445,144 A | 8/1995 | Wodicka et al. |
| 5,868,682 A | 2/1999 | Combs et al. |
| 2003/0034035 A1 | 2/2003 | Raphael |

OTHER PUBLICATIONS

Raphael, DT, "Acoustic Reflectometry Profiles of Endotracheal and Esophageal Intubation" Anesthesiology, vol. 92, No. 5, pp. 1293-1299, May 2000.

European search report for corresponding European application 07753539.1 lists the references above.

International Search Report dated Feb. 20, 2008.

Berman, L.S. et al. 1988. "Capnographic detection of anaesthesia circle valve malfunctions." Can J Anaesth. 35(5):473-475.

Brooks, L.J. et al. 1983. "Reproducibility and accuracy of airway area by acoustic reflection." Airway Area by Acoustic Reflections. Children's Hospital, Boston 02115; and the Biomechanics Institute, Boston, Massachusetts 02215. 777-787.

Flynn, P.J. et al. 1984. "Inspired humidity in anesthesia breathing circuits: comparison and examination of effect of Revell circulator." Can Anaesth Soc J. 31(6):659-663.

Fredberg, J.J. et al. 1978. "The distributed response of complex branching duct networks." J. Acoust. Soc. Am. 63(3):954-961.

Fredberg, J.J. 1978. "A modal perspective of lung response." J. Acoust. Soc. Am. 63(3):962-966.

Fredberg, J.J. et al. 1979. "Airway area by acoustic reflections measured at the mouth." Acoustic Inferences of Airway Area. Cambridge Collaborative, Inc., Cambridge 02142; Department of Medicine (Pulmonary Division), Children's Hospital medical Center, and Department of Pediatrics, Harvard Medical School, Boston, Massachusetts 02115. 749-758.

Goupillaud, P.L. 1961. "An Approach to Inverse Filtering of Near-Surface Layer Effects From Seismic Records." Geophysics. XXVI(6):754-560.

Kumar, A.Y. et al. 1992. "Equipment: Inspiratory valve malfunction in a circle system: pitfalls in capnography." Can J Anaesth. 39(9):997-999.

Louis, B. et al. 1994. "Pulmonary airway area by the two-microphone acoustic reflection method." Two-Microphone Acoustic Reflection Method. American Physiological Society. 2234-2240.

Mansfield, J.P. et al. 1995. "Using Acoustic Reflectometry to Determine Breathing Tube Position and Patency." Journal of Sound and Vibration. 188(2):167-188.

Raphael, D.T. et al. 1989. "Resonance Mode Analysis for Volume Estimation of Asymmetric Branching Structures." Annals of Biomedical Engineering. 17:361-375.

Raphael, D.T. 1987. "An explicit resonance condition for a rigid symmetric $N$th-order branching network." J. Acoust. Soc. Am 83(1):335-337.

Raphael, D.T. et al. 1987. "Volume estimation of symmetrical branching structures by resonance mode analysis." J. Acoust. Soc. Am. 82(3):800-806.

Raphael, D.T. 2007. "Acoustic reflectometry imaging of the airway." Seminars in Anesthesia, Perioperative Medicine and Pain. 26:210-217.

Schroeder, M.R. 1966. "Determination of the Geometry of the Human Vocal Tract by Acoustic Measurements." 41(4)(2):1002-1010.

Ware, J.A. et al. 1968. "Continuous and Discrete Inverse-Scattering Problems in a Stratified Elastic Medium. I. Plane Waves at Normal Incidence." Inverse-Scattering Problems. The Journal of the Acoustical Society of America. 911-921.

FREQUENCY-BASED METHODS, SYSTEM AND APPARATUS FOR CAVITY RECONSTRUCTION VIA AREA-DISTANCE PROFILES

CROSS-REFERENCES

This application claims priority to U.S. Provisional Application 60/783,740 filed on Mar. 17, 2006, the content of which is incorporate herein in its entirety by reference

FIELD OF THE INVENTION

The present invention, in general, relates to the measurement of cavities of interest using acoustic signals. It also relates to a modified circle system that facilitates such measurement. More specifically, the invention provides a method, system and apparatus for performing acoustic resonance-based creation of an area-distance profile of a cavity.

BACKGROUND OF THE INVENTION

Acoustic pulse reflectometry is a non-invasive technique for determining the internal dimensions of a duct of variable cross-section. A generated acoustic pulse propagates down a reflectometer wavetube into the cavity of interest. The pressure amplitudes of the acoustic reflections are analyzed, so as to generate the input impulse response, which in turn allows the calculation of the cross-sectional area as a function of axial distance. The resulting area-distance curve, which consists of an equivalent acoustic area of the cavity versus axial length down the cavity, serves as a "one-dimensional image" of the cavity of interest.

In medical context, this capability may be used to distinguish signals arising from body cavities, such as the trachea and the esophagus because the characteristic area-distance profile are quite different from these two structures. For example, for a human endotracheal tube (ETT) airway cavity, the profile shows a constant cross-sectional area throughout the length of the ETT followed by an increase in the cross-sectional area corresponding to the increase of area of more distal part of the lung. During human esophageal intubation, the profile shows a constant cross-sectional area throughout the length of the ETT, followed by a sudden decrease in the cross-sectional area. This occurs because the nonrigid human esophagus is soft and collapses around the distal end of the ETT, thereby preventing further transmission of the acoustic impulse down the cavity.

Because acoustic reflectometry is based on physical principles, it does not rely on detection of carbon dioxide to distinguish between an esophageal and an endotracheal intubation. This is vital in the cardiopulmonary arrest setting when capnography may be useless because the patient has little or no pulmonary circulation and, therefore, may not produce a detectable amount of exhaled carbon dioxide.

Figure 11:
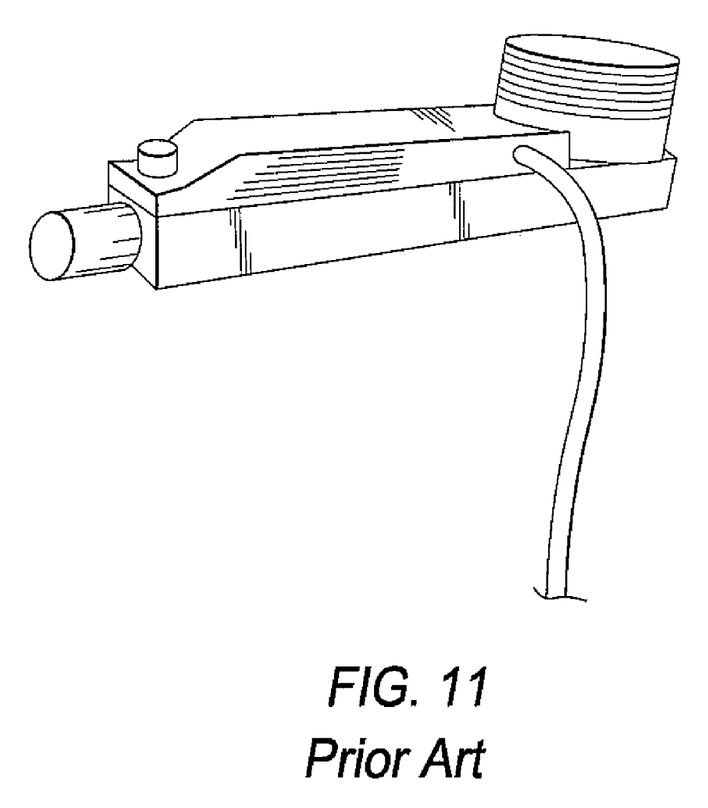
FIG. 11 shows a prior art acoustic reflectometer.

The current art, Hood Labs reflectometer (Pembroke, Mass.), shown in FIG. 11, uses an internal wavetube, which is connected to a duct that is to be explored. When repetitive impulses are emitted from the reflectometer, the impulses emerge from the wavetube, traverse through the duct, and are reflected back toward the wavetube, where they are reflected further still within the wavetube. The Hood Labs time-domain acoustic pulse pressure reflectometer uses a series of equally spaced impulses of 0.2 ms duration. It uses the well-known Gopillaud-Ware-Aki (GWA) algorithm to keep track of the course of the emitted impulses and of their reflections, whether reflected from the duct (single and higher order internal duct reflections) or internally reflected within the wavetube.

Currently available acoustic reflectometers (ARs) are generally of two types: single-microphone AR and two-microphone AR. The major limitation of the single-microphone GWA algorithm-based AR is its unwieldiness, which is due to the long wavetube required to separate the duct reflection from the unwanted source reflection. Such a bulky single-microphone AR system is essentially unusable in the limited space confines offered by an operating room or an ICU.

For the two-microphone AR, the initialization of such a system is integrated with the GWA algorithm which demands that the inherent instability in the system be addressed by making the first non-zero pressure to be larger than some minimal value. Although a correction procedure may be used to correct the error introduced by this threshold, as the distance between the two microphones is reduced, the instability of the algorithm is inevitably increased. The inherent instability of the two-microphone algorithm significantly limits miniaturization of such a device.

Therefore, there still exists a need for a better approach to the design of AR that is simple, small, portable, fast and reliable such that the device may be practically employed in locales with minimal work space. Current art devices cannot be used for a prolonged period of time in a patient humidified breathing circuit, and require detachment of the breathing tube in order to obtain an area-distance profile.

SUMMARY OF THE INVENTION

In light of the needs for an improved acoustic reflectometer, it is one object of the present invention to provide a broadly applicable acoustic reflectometry method, system and apparatus that allow satisfactory area-distance reconstruction of the cavities of interest. The method, system and apparatus of the present invention do not utilize acoustic pulses, but can use continuous waves. It can also make use of the overtones making it possible to estimate the contributions from the secondary and higher order reflections. The resulting form of the reflection coefficients will hence be comparable to those obtained by the GWA algorithm. One advantage it has over current art devices is that it does not require a wavetube for proper operation.

It is also an object of the present invention to provide a method of manufacture, system and apparatus for a circle system that allows for the connection of extra devices like exemplary embodiments of the present invention. It places the inspiratory valve close to the device to be attached and the expiratory valve closer to the endotracheal tube. This placement of valves creates a space between the inspiratory and expiratory valve that has a column of cold dry gas. One advantage of this arrangement is that it prevents exhaled gas with water vapor from entering the attached device. As a result, the device is made resistant to the effects of humidification.

In one aspect, the present invention provides an acoustic resonance-based device that utilizes the iterative resonance equivalent-length (IREL) method, which analyzes the resulting interaction (standing waves) between the generated and reflected signals at the open end in a time-gated manner, in order to determine the area ratio between adjacent segments at a specific distance within the cavity. Additional measures to enhance the area ratio calculation include considerations of phase, signal inversion, and anti-resonance.

In another aspect, the present invention also provides a method for creating, by performing of the IREL method, an area-distance profile of a cavity.

In yet another aspect, the present invention also provides a method for modifying a breathing circuit, which incorporates an acoustic resonance-based device according to embodiments of the present invention, in such a way that a measurement can be obtained at end-exhalation when the inspiratory and expiratory valves are both closed. This is the optimal time for such a measurement within a mechanical ventilation system that is connected to a breathing circuit with moving valves. This technique prevents sound leakage through the valves, and allows a direct straight line measurement from the resonance device to the interior of a cavity.

Embodiments of the present invention include the incorporation of an acoustic reflectometer within a breathing circuit such that no detachment of the breathing tube is required Such embodiments are resistant to the effects of breathing circuit humidification, pressure and temperature variations.

Other aspects and advantages of the invention will be apparent from the following description and the appended claims.

DETAILED DESCRIPTION

In order to develop a small circuit-embeddable reflectometer, there should ideally be no wavetube. The GWA algorithm in its original conception by geophysicists does not require a wavetube. All that is necessary is the ability to characterize the reflections associated with any one specific impulse. Presently the reflections are allowed to die out quickly enough from one impulse to the next.

A study medium that can be used to develop the exemplary embodiments of the present invention can be a stratified medium composed of multiple layers, each of which is characterized by a constant length. Exemplary embodiments of the present invention developed using this medium can be modified by one of ordinary skill in the art for use on other systems, for example, humans or animals.

The present invention will now be described in detail by referring to specific embodiments as illustrated in the accompanying figures.

Frequency Considerations

Consider the class of all periodic function $f(t)=\Sigma \alpha_n e^{in\omega t}$. The average power in one period $(-\pi/\omega_0, \pi/\omega_0)$ of a component sinusoidal function is $$\overline{f(t)^2}=(\omega/2\pi)\int f^2(t)dt=\Sigma |\alpha_n|^2$$

For a finite energy signal $f(t)$, its Fourier integral is given by $F(\omega)=A(\omega)e^{i\Phi(\omega)}$. The inverse transform of the energy spectrum is $E(\omega)=A^2(\omega)$, which is known as the autocorrelation, which is taken as a frequency integral from $-\infty$ to $\infty$.

$$\rho_f(t)=(1/2\pi)\int A^2(\omega)e^{i\omega t}d\omega=(1/2\pi)\int A^2(\omega)\cos \omega t d\omega$$

The power spectrum P(ω) of a function f(ω) is defined as the Fourier transform of its autocorrelation R(t), where $$P(\omega)=\int R(t)\cos \omega t dt \text{ and } R(t)=(1/2\pi)\int P(\omega)\cos \omega t d\omega$$

Figure 1A:
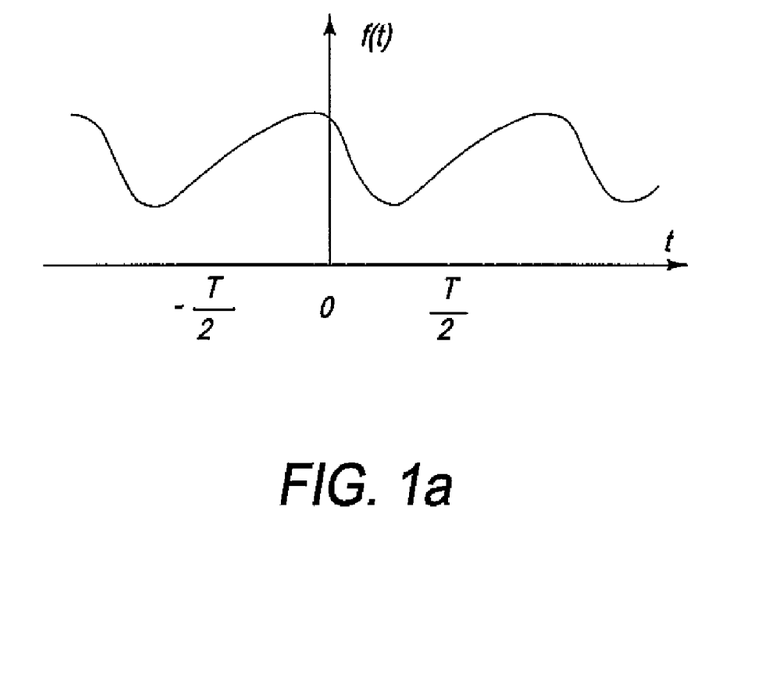
FIG. 1a shows a graph of an exemplary periodic function f(t) with a period of T.

Consider a periodic function of period T, as shown in FIG. 1a, $$f(t)=\Sigma \alpha_n e^{in\omega t} \text{ with } \omega_0=2\pi/T$$

Figure 1B:
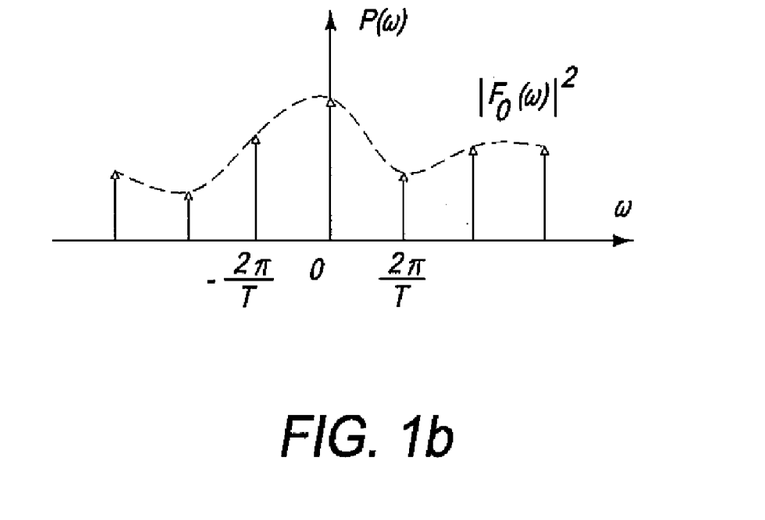
FIG. 1b shows a graph of the power spectrum P(ω) of f(t).

Its power spectrum P(ω) is a sequence of equidistant pulses, as shown in FIG. b.

$$P(\omega) = 2\pi |\alpha_0|^2 \delta(\omega - \omega_0) \text{ where } \alpha_n = \frac{F_0(n\omega_0)}{T}$$

Figure 2:
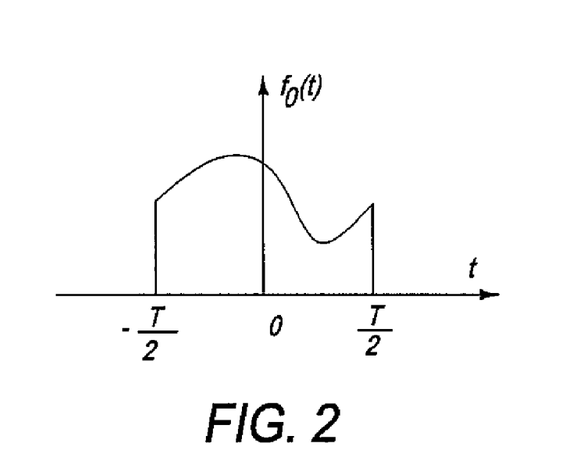
FIG. 2 shows a graph of a time limited slice $f_o(t)$ of f(t).

If the above function is time-limited, as shown in FIG. 2, the Fourier transform is given by $|F_0(\omega)|$, and the power spectrum P(ω) is given by $$P(\omega)=(2\pi/T^2)|F_0(\omega)|^2\Sigma\delta(\omega-n\omega_0)$$

for n=1, 2, 3, ...

Embodiments of the present invention that employ the spectral considerations differ from conventional time-domain acoustic reflectometry and allow a satisfactory area-distance reconstruction of the cavity of interest. For example, they may differ in that they do not necessarily require acoustic pulses, but may use continuous waves.

Resonance Considerations in Branching Structures

When fluid in a branching duct is driven by a vibrating piston, waves are transmitted and reflected throughout the structure. The multiple reflections at the bifurcations generate waves traveling in the opposite direction that, upon interacting with the incident waves, lead to the production of standing waves. The resulting stationary oscillations are related to the phenomenon of resonance.

The lung is a cavity that can resonate at different frequencies when subjected to an acoustic sound source, such as a loudspeaker. A great number of different resonance frequencies are observed because of the complex branching network within the lung. These multiple resonance frequencies depend on the individual lengths and cross-sectional areas of the various branches.

Resonance is defined as that frequency at which the reactive component of the input impedance vanishes. Consider FIG. 3, which shows a symmetrical branching cylindrical duct with two orders of bifurcations.

Figure 3:
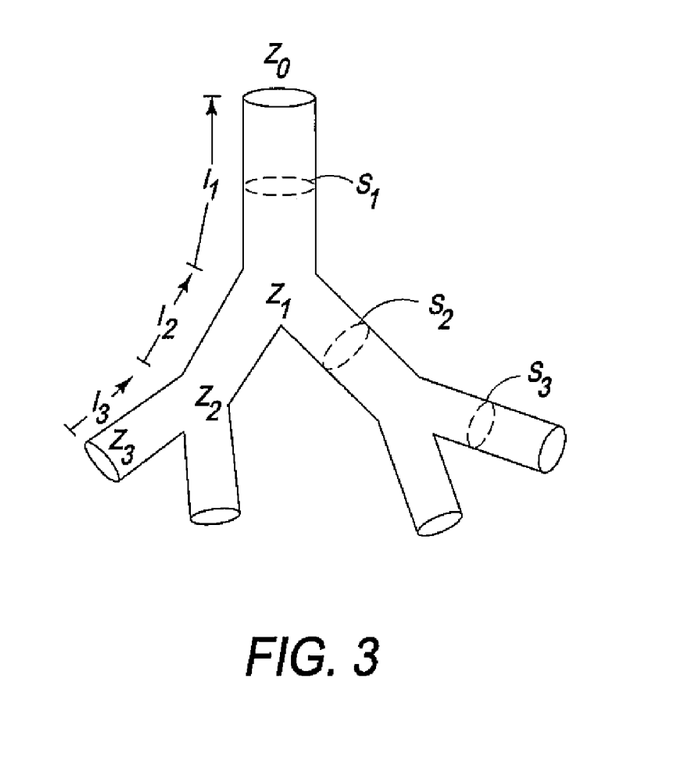
FIG. 3 shows a symmetrical branching cylindrical duct with two orders of bifurcations.

The individual branches are of length $l_1$ and cross-sectional areas $S_i$, for i=1, 2, 3 . . . . The point at $z_0$ is open-ended, whereas the distal ends $z_3$ of each terminal branch are rigid and closed. The resonance condition used in one or more exemplary embodiments of the present invention have been derived for this rigid symmetric second-order branching structure, i.e., Eq. 1:

$$l_1 + k^{-1}\tan^{-1}\left(\left(\frac{2S_2}{S_1}\right)\tan k\left(l_2 + k^{-1}\tan^{-1}\left(\left(\frac{2S_3}{S_2}\right)(\tan k)l_3\right)\right)\right) = \frac{(2n-1)\pi}{2k}$$

for n=1, 2, 3, ... and where k is the wave number (k=2πf/c), f is the frequency, and c is the speed of sound.

The resonance condition for the general case of a rigid symmetrical branching network involving an arbitrary number, N, of nodal orders of bifurcation has been derived as well and can be used in one or more exemplary embodiments of the present invention. Consider the Nth order symmetrical branching network of FIG. 4.

Figure 4:
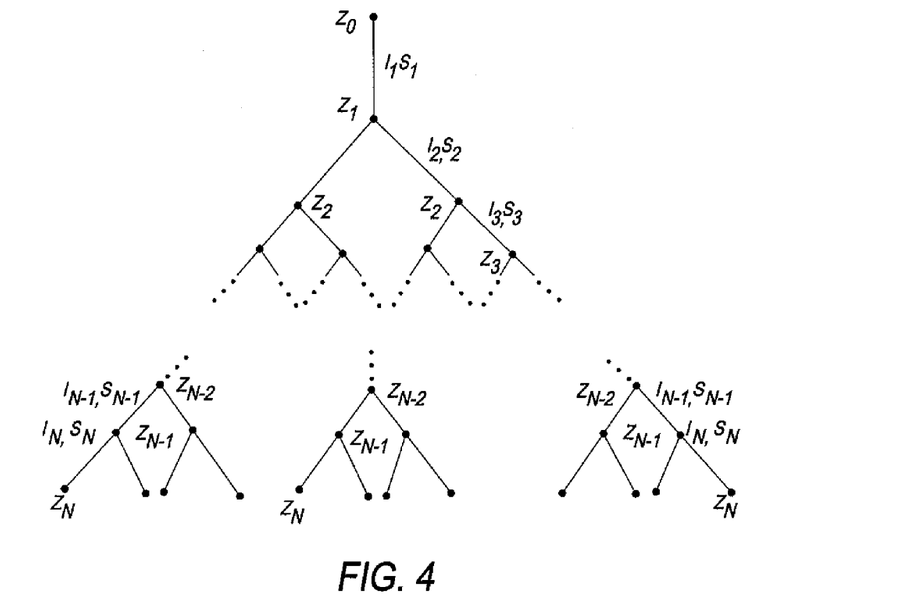
FIG. 4 shows a schematic diagram depicting an Nth order symmetric branching network in accordance with the present invention.

At any given level of bifurcation, the branches are characterized by a length $l_i$ and $S_i$ for i=1, 2, 3, .... The complete Nth order resonance condition is Eq. 2: for Multiply Bifurcated Structure $$l_1 + k^{-1}\tan^{-1}\left(\left(\frac{2S_2}{S_1}\right)\tan\left(l_2 + k^{-1}\tan^{-1}\left(\left(\frac{2S_3}{S_2}\right)(\tan k)\left[l_3 + \ldots + k^{-1}\tan^{-1}\left(\frac{2S_N}{S_{N-1}}\right)(\tan k)l_N\right]\right)\right)\right) = \frac{(2n-1)\pi}{2k}$$

with n=1, 2, 3, ...

The transcendental eigenvalue equations, given by Eqs. 1 and 2, explicitly illustrate the relationship between the wave number, the branch dimensions, and the harmonic number. When n=1, the fundamental frequency occurs. When n>1, the resonant overtones occur as quasi-odd multiples of the fundamental frequency, but no quasi-even harmonics occur.

Proceeding from the most distal branch $l_N$, each successive branch is modified by a pair of area-weighted tangent and inverse-tangent functions that, when added to the true length of the immediately adjacent proximal branch, serve as the basis for the next higher area-weighting and tangent-inverse tangent modifications. In essence, this is an area-weighted trigonometric operator that operates on the overall effective length of all branches distal to a given node. The degree to which a branch is successively embedded within the argument of the nested tangent-inverse tangent functions reflects its nodal order within the hierarchy of branches.

The resonance conditions for asymmetric branching structures have been derived in the present invention and can be used in one or more exemplary embodiments of the present application. These can be used by exemplary embodiments of the present invention to accurately estimate the volumes of glass model and other branching structures with a frequency-based approach.

With these spectral and resonance considerations in mind, exemplary embodiments in accordance with the present invention are presented.

A Resonance Reflectometry Inverse Algorithm

An Operator Formalism for Resonance-Based Duct Reconstruction

An area-weighted frequency-dependent operator is defined as $$P_i = k^{-1}\tan^{-1}\left(\left(\frac{S_i}{S_{i-1}}\right)\tan k\right)$$

that operates on an equivalent length $l_e$, distal to the interface between segments $S_i$ and $S_{i-1}$, i.e., $$P_i l_e = k^{-1}\tan^{-1}\left(\left(\frac{S_i}{S_{i-1}}\right)(\tan k)l_e\right)$$

The operator P has an inverse operator $$P_i^{-1} = k^{-1}\tan^{-1}\left(\left(\frac{S_{i-1}}{S_i}\right)(\tan k)\right),$$

with which it is operationally symmetric, i.e., $PP^{-1}=P^{-1}P$. Note the inversion of the area ratio in the inverse operator.

This formalism helps to simplify the form of the equations that follow.

Resonance Conditions for a Duct Composed of Cylindrical Segments

In the GWA formulation of acoustic pulse reflectometry, it is desirable to separate the incident and the reflected pulses.

In the exemplary embodiment in accordance with the present invention, in resonance-based reflectometry, it is desirable that the incident and the reflected pulses interact.

In an exemplary embodiment of the present invention, an iterative resonance equivalent-length (IREL) method has been developed. Assume the duct is a tubular object composed of N joined cylindrical segments of variable cross-sectional area $S_i$ and of length $l_i$. With the IREL method, it is possible to solve for the individual successive cross-sectional area ratios between adjacent cylindrical segments with the use of the observed frequency spectrum at the open end. The IREL reconstruction method is a hybrid approach that (a) uses a resonance-based iterative solution to generate the values of the area ratios between adjacent cylindrical segments, but (b) considers the added information obtained from observing the spectral changes associated with frequency-specific sinusoidal input functions.

In another exemplary embodiment in accordance with the present invention an Iterative Resonance-Based Equivalent Length Method for Duct Area-Distance Profile Reconstruction with equal length segments $l_1=l_2=l_3=l_4=\ldots=l_{N+1}$ has been developed. In a manner analogous to pulse reflectometry, this embodiment of an iterative resonance-based reconstruction algorithm assumes the following:

(1) Modeled Structure: A tubular object is composed of N+1 cylindrical segments of cross-sectional area $S_{N+1}$, but of equal length segments $l_1=l_2=l_3=l_4=\ldots=l_{N+1}$. The total travel time (from any one interface to the next and back) is $T_1=2l_1/c$.

(2) Open Proximal End: An open end exists at the proximal mouth of segment $l_1$, where the microphone and loudspeaker are located.

(3) Duct Open or Closed: An area-weighted trigonometric operator is applied to each successive segment whether the duct is open or closed at its distal end. The only term that is affected by the openess/closedness of the distal duct is $m=(2n-1)\pi/2k$. If the distal ends are rigid, quasi-odd harmonics are expected, and if distal ends are open, quasi-even harmonics of the form $(2n)n/2k$, with $n=1, 2, 3, \ldots$ are expected. For unknown structures, as a measure of the degree of closedness (or openness) of the distal part, it can be assumed that an approximate measure is a linear combination of resonance and antiresonance, i.e., $m=[(2n-1)\mu+(1-\mu)(2n)]n/2k$, $0<\mu<1$, $n=1, 2, 3, \ldots$. This value can be estimated by comparing the ratios of the observed values for successive resonance frequencies.

Step I: Sound the Duct and Obtain the Frequency (Resonance) Spectrum

The cavity is open-ended proximally and is closed distally at some maximal distance L. The lossless duct is sounded with, say, a white-noise sound source, so as to obtain the frequency (resonance) spectrum. The lowest observed frequency corresponds to the maximal depth L, and is defined by the relation $f=c/4L$, or $L=c/4f$ as a working first estimate. One approach is to make the individual probe frequencies as integral multiples of the fundamental frequency. Another approach, which we shall follow herein, is to divide the length L of the cavity into N+1 segments, with any given interfaces separated from its neighbor by a constant step length $1_1=L/N$.

Step II: Determine the Area Ratio at First Interface by Iterative Resonance Approach For illustration, consider the simplest single interface problem composed of two segments $1_1$ and $1_2$, with a rigid boundary at total length $L=1_1+1_2$. It is assumed in this algorithm that the first cylindrical segment is of known area $S_1$ and $1_1$, whereas the area of the second segment, $S_2$, is unknown; however, the actual length of the second segment is $1_2=L-1_1$, with L as determined from sounding the duct. T is the two-way travel time to the first interface and back. At time 2T, we expect the arrival of the reflected wave from the interface at $x=L$, which allows the formation of a standing wave to occur at $x=0$. Hence, the single interface problem (for n=1, the fundamental frequency) simplifies to $$(S_2/S_1)\tan k1_2 \tan k1_2=1,$$

with an equivalent acoustic length for the structure of $$l_1 + P_2(L - l_1) = \pi/2k$$

$$\text{with } P_2 = k^{-1}\tan^{-1}\left(\left(\frac{S_2}{S_1}\right)\tan k\right)$$

$n=1, 2, 3, \ldots$ The area ratio $$\left(\frac{S_2}{S_1}\right)$$

can then be solved, which can be shown to be $$S_2/S_1=1/(\tan k1_1)\tan k(L-1_1)$$

Note that $S_2$ is the area associated with the segment $L-1_1$. The reflection coefficient from the interface at $x=1_1$ is $$r = \frac{(S_1 - S_2)}{(S_1 + S_2)} = \frac{((\tan kl_1) \tan k(L - l_1) - 1)}{((\tan kl_1) \tan k(L - l_1))}$$

Step III: Determine the Area Ratio at First Interface by Power Spectrum Approach The information provided in Step II can be supplemented by information garnered from frequency-specific sinusoidal functions. One is an initial wave of frequency $f=c/4l_1$ to probe the interface at $x=1_1$. Assume that the initial wave is a sinusoidal wave $f_i(t)=A \cos(\omega_0 t-kx)$. At $x=0$, its power spectrum is $$P(\omega)_r = \left(\frac{\pi B^2}{2}\right)[\delta(\omega - \omega_0) + \delta(\omega + \omega_0)]$$

At $x=0$, the reflected wave $f_r(t)=B \cos(\omega_0 t+kx)$ has a power spectrum $$P(\omega)_r = \left(\frac{\pi B^2}{2}\right)[\delta(\omega - \omega_0) + \delta(\omega + \omega_0)]$$

At the interface, $B/A=(S_1-S_2)/(S_1+S_2)$ and the power reflection coefficient should be $$r=(S_1-S_2)^2/(S_1+S_2)^2$$

The reflected signal power spectrum is compared to the input signal power spectrum in the frequency interval about $f_1$, and the reflection ratio $r_1$ is calculated.

The power spectrum reflects the frequency content in a frequency interval centered about $f=c/4l_j$. Resonance will be prominent when the incident wave encounters a dense medium at $x=1_j$, which results in a reflected wave with only a slight reduction in amplitude and no change in phase; hence, the amplitude of the standing wave at the open end is almost double that of the incident wave (an antinode). On the other hand, if the reflection is from a rarefied medium, the reflected wave will be of lesser amplitude.

Consider a duct of length L terminated at one end. Assume that the generated wave at $x=0$ is of amplitude A, and that the reflected wave is of $Be^{j\theta}$. The combined standing wave at $x=0$ has a pressure amplitude of $$P=\{(A+B)^2\cos^2[k(L-x)-\theta/2]+(A-B)^2\sin^2[k(L-x)-\theta/2]\}^{1/2}$$

A frequency-specific probe, with a properly adjusted phase ($\theta=\pi$ radians in this terminated duct example), will produce an antinode at $x=0$, with a resulting pressure amplitude maximum of $P_{max}=A+B$. This approach can be extended to more structures involving single or multiple interfaces. By probing each interface with a potentially resonance-producing test frequency, maximization of reflection coefficients is achieved.

For the multiple-segment problems discussed below, an iterative solution is provided to the general problem of a structure composed of an arbitrary number of different sized cylindrical ducts. Modeling is simplified if it is assumed that the lengths (but not the areas) of the ducts are equal. For each example, the solution is first derived for a specific number of ducts of arbitrary length, and the corresponding solution to the fixed step length requirement ($1_1=1_2=1_3 \ldots$) follows.

Step IV: Resonance Iterative Technique: Multiple Interface Problem

Two Interfaces: Three Cylindrical Ducts

The two-interface problem involves a structure with three cylindrical ducts. At time T, the $S_1$-$S_2$ interface is studied with frequency $f_1$ as in steps II-III. The receiver is then made blind to the effects of any higher order reflections from frequency $f_1$.

At time 2T, the resonance-producing reflection from the second interface located at $x=1_1+1_2=21_1$ is examined. For this distance to the interface, $21_1=c(2T)$ and $\lambda_2=4(2l_l)$. This distance information from the open end to the interface of interest determines the specific exciting frequency $f_2=c/\lambda_2$. For the fundamental frequency (n=1), the equivalent acoustic length of the tubular object (inclusive of segment $1_3$ with area $S_3$), is $$1_1+P_2(1_2+P_31_3)=\pi/2k_2$$

or, since $1_1=1_2=1_3$, $$1_1+P_2(1_1+P_31_1)=\pi/2k_2$$

with $P_2=k_2^{-1}\tan^{-1}((S_2/S_1)\tan k_2)$ and $P_3=k_2^{-1}\tan^{-1}((S_3/S_2)\tan k_2)$.

$S_2/S_1$ has been previously studied as in Steps II-III. With successive applications of the inverse operator, the solution to the interface surface ratio encountered with arbitrary step lengths is $$\frac{S_3}{S_2} = \frac{\tan k_2(P_2^{-1}(m_2 - l_2) - l_1)}{\tan k_2 l_3}$$

For the fixed step length model, the step lengths are equal, $1_1=1_2=1_3$. The fixed step length solution becomes $$\frac{S_3}{S_2} = \frac{\tan k_2(P_2^{-1}(m_2 - l_1) - l_1)}{\tan k_2 l_1}$$

Therefore, $(S_3/S_2)$ is the area ratio at the distance $x=21_1$, where $P_2^{-1}=k_2^{-1}\tan^{-1}((S_1/S_2)\tan k_2)$. A different exciting frequency $f_2=c/\lambda_2$ is used for the second interface. It travels a distance $x_2=2(cT)$ and back. It is sensitive only to the effect of $f_2$ and its contribution at the receiver. The reflected signal power spectrum is compared to the input signal power spectrum in the frequency interval about $f_2$. Using the prior $r_1$, the reflection ratio $r_2$ is now calculated.

As discussed below, the contribution from the $S_2$-$S_3$ interface is compared to other interface contributions, including the $S_1$-$S_2$ interface, and it is scaled on the basis of its relative frequency-specific power spectra. If the surface $S_3$ is not a terminating distal surface for the structure, a further correction must be made to take into account more cylindrical segments.

Three Interface Problem (Four Cylindrical Segments)

Similarly, the three interface problem has a general equivalent length formulation of $$1_1+P_2[1_2+P_3(1_3+P_41_4)]=(2n-1)\pi/2k_3=m_3,$$
$$n=1, 2, 3, \ldots$$

The fixed step length formulation requires that $1_1=1_2=1_3=1_4$, four segments of equal length, so that $$1_1+P_2[1_1+P_3(1_1+P_41_1)]=(2n-1)\pi/2k_3=m_3,$$
$$n=1, 2, 3, \ldots$$

with distance to the interface, $1_1+1_2+1_3=31_1=c(3T)$, and wave number $k_3=2\pi\lambda_3$ with $\lambda_3=4(1_1+1_2+1_3)=4(31_1)$. The exciting probe frequency is set at $f_3=c/\lambda_3$. Using inverse operators, the inverse solution for the area ratio at the distal $S_4/S_3$ distal interface is shown to be $$\frac{S_4}{S_3} = \frac{\tan k_3(P_3^{-1}(P_2^{-1}(m_2 - l_1) - l_1) - l_1)}{\tan k_3 l_1}$$

where $P_3^{-1}=k_3^{-1}\tan^{-1}((S_2/S_3)\tan k_3)$ and $P_2^{-1}=k_2^{-1}\tan^{-1}((S_1/S_2)\tan k_2)$. $(S_4/S_3)$ is the area ratio at the distance $x=1_1+1_2+1_3=31_1$.

The receiver is now made blind to the reflection of $f_1$ and $f_2$, and is sensitive only to the effects of $f_3$. The reflected signal power spectrum is compared to the input signal power spectrum in the frequency interval about $f_3$. Using the prior $r_1$ and $r_2$, the reflection ration of $r_3$ is now calculated. An attenuator can be used to silence unwanted reflections.

The contribution from the $S_3$-$S_4$ interface is compared to other interface contributions, and is scaled with respect to relative frequency-specific power. If $S_3$ is not a terminating distal surface, additional cylindrical segments are considered.

Nth Order Interface Problem (N+1 Cylindrical Segments)

The total travel time for a resonance-producing reflection from the Nth interface is NT, corresponding to a distance of $x_N=\Sigma l_i(i=1, \ldots N)$, for which wave number $k_N=2\pi\lambda_N$, $\lambda_N=4(1_1+1_2+\ldots+1_N)$, The exciting probing fundamental frequency is $f_N=c/\lambda_N$. The equivalent acoustic length of the tubular object of N+1 cylindrical segments with N interfaces is $$1_1+P_2\{1_2+P_3[1_3+P_4(1_4+\ldots+P_N1_{N+1})]\}=$$
$$(2n-1)\pi/2k_N$$

with n=1 for the fundamental, and n>1 for higher order harmonics. Successive frequency-weighted inverse operators allow calculation of the area ratios at successive interfaces. As before, with $m=\pi/2k_N$ (fundamental), the Nth interface area ratio can be calculated from $$\frac{S_{N+1}}{S_N} = \frac{\tan k_N [P_N^{-1}\{P_{N-1}^{-1}(m_N - l_1) - l_2\} - l_3 \ldots - l_{N-1}] - l_N}{\tan k_N l_{N+1}}$$

For the fixed step-length model, with all lengths equal, the corresponding solution for the area ratio is $$\frac{S_{N+1}}{S_N} = \frac{\tan k_N [P_N^{-1}\{P_{N-1}^{-1}(m_N - l_1) - l_1\} - l_1 \ldots - l_1] - l_1}{\tan k_N l_1}$$

where $P_N^{-1}=k_N^{-1}\tan^{-1}((S_{N-1}/S_N)\tan k_N)$, $P_{N-1}^{-1}=k_{N-2}^{-1}\tan^{-1}((S_{N-2}/S_{N-1})\tan k_{N-1})$. Nth order harmonics can also be utilized, with $m=(2n-1)\pi/2k_N$ and n>1.

Figure 10:
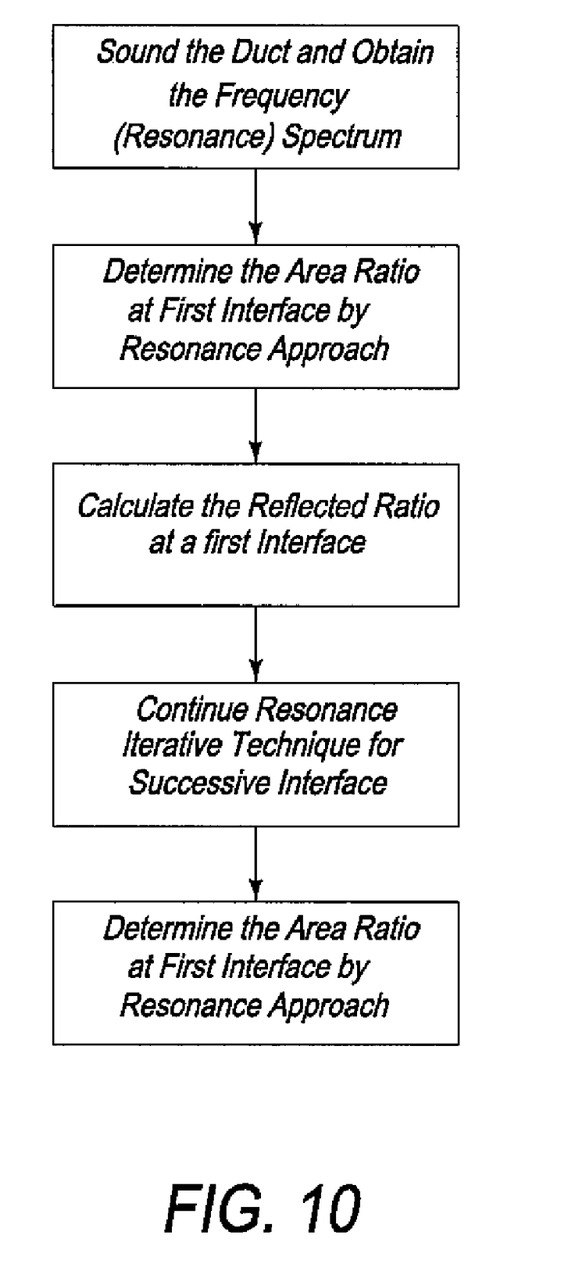
FIG. 10 shows a flow diagram depicting an exemplary embodiment in accordance with the present invention.

In summary, the above presented exemplary embodiment in accordance with the present invention is an outline for an iterative resonance-based method for duct area-distance profile reconstruction. FIG. 10 shows a general flow diagram of a method according to embodiments of the invention as described above. Only the cross-sectional area $S_1$, and the length of the first cylindrical segment $1_1$, are known a priori. The length of the first segment $1_1$ is the distance between all successive adjacent interfaces. Once the duct length L has been calculated, the step length is calculated as L/N. Using the IREL algorithm, the area ratio at a given interface is determined, and it is compared and scaled relative to other interface ratios. The assumption of a fixed step length approach used in the IREL method is similar to the assumption of a constant travel time within any given layer in the GWA approach.

Perfect Resonance

For the two-interface (three segment) cylindrical problem, the expected reflection coefficient r observed at $x=0$ is $r=(1-r_1^2)r_2$, where $r_1$ is the reflection coefficient at $x=1_1$ and $r_2$ is the reflection coefficient at $x=1_1+1_2=2l_1$. If perfect resonance occurs at the second interface, the signal is completely reflected, such that $r_2=1$. When this occurs, $r=(1-r_1^2)$ with $r_1=(\phi-1)/(\phi+1)$ and $\phi=(\tan kl_1)(\tan kl_2)=\tan^2 kl_1$.

Imperfect Resonance/Partial Transmission

If the reflection is not perfect at $x=2l_1$, transmission occurs beyond the point at $x=2l_1$ into a third duct component of area $S_3$. The effective reflecting surface available at $x=1_1$ is $S_2^*=S_2-S_3$. The corrected reflection coefficient $r_1$ at $x=1_1$ becomes $r_1^*=[S_1-(S_2-S_3)]/[S_1+(S_2-S_3)]$, where $S_3$ is unknown. Using the observed reflection response, this can be manipulated into $S_3[(S_1-S_2)-r_1^*(S_1+S_2)]/[r_1^*-1]$.

This value for $S_3$ can now be used for the next iteration.

Power Spectra Approach

In another exemplary embodiment of the present invention the isolation of the reflection contribution from the nth interface is of interest, a digital sweep composed of multiple successive wavelength-based probes is used. Each successive wavelength-based sweep component exhibits sound with a wavelength that is an integral multiple of the calculated step length. Each successive probe has as its central wavelength $\lambda_n=4n1_l$ (frequency $f_n=c/4n1_1$), $n=1, 2, \ldots, N$. Hence, each successive component probe of the sweep detects resonance only in the small length about the interface at $x=\lambda_n=4nl_l$, and it is allowed to decay before the next probe of $\lambda_{n+1}=4(n+1)1_1$ is initiated.

Consider an initial wave of frequency $f=c/41_1$ that is used to probe the interface at $x=1_1$. Assume that the initial wave is a sinusoidal wave $f_i(t)=A\cos(\omega_0 t - tx)$. At $x=0$, its power spectrum is $$P(\omega)_i = (\pi A^2/2)(\delta(\omega-\omega_0)+\delta(\omega+\omega_0))$$

At $x=0$, the reflected wave $f_r(t)=B\cos(\omega_0 t - tx)$ has a spectrum $$P(\omega)_r = (\pi B^2/2)(\delta(\omega-\omega_0)+\delta(\omega+\omega_0))$$

At the interface, $B/A=(S_1-S_2)/S_1+S_2)$.

But this is just the reflection coefficient from the first interface, $$r=(S_1-S_2)/(S_1+S_2)$$

from the first interface.

Successive use of frequency amplitudes from the power spectra intervals centered about successive probe frequencies $f_i=c/\Sigma 1_i$ should allow, in conjunction with the Iterative Resonance Equivalent Length approach described above, the determination of the successive interval reflection coefficients needed for construction of the area-distance profile.

The conventional GWA method uses an impulse composed of multiple frequencies. However, component sinusoidal waves of the GWA impulse will exhibit variations of amplitude at certain distances into the cavity, thus altering the form and the amplitude of the impulse at those distances. This affects the return signal measured at the receiver.

Within the present IREL embodiment, this problem is avoided because the timing for each frequency-specific signal is such that the amplitude is maximized upon its return to the receiver.

When successive fundamental resonance probe frequencies are employed, as in the IREL method and the power spectra approach, only the primary reflection is taken into account, whereas secondary and higher order reflections are excluded.

Hence, when the IREL approach is employed, the expected total resonance response $R_i$ at the open end at time intervals ($i=1, 2, 3, \ldots$), in terms of the reflection coefficients $r_i$ should be $$R_0 = r_0$$

$$R_1 = r_1(1-r_0^2)$$

$$R_2 = r_2(1-r_0^2)(1-r_1^2)$$

$$R_3 = r_3(1-r_0^2)(1-r_1^2)(1-r_2^2)$$

which will allow one to solve sequentially for the interface reflection Coefficients $$r_0 = R_0$$

$$r_1 = R_1(1-r_0^2)^{-1}$$

$$r_2 = R_2[(1-r_0^2)(1-r_1^2)]^{-1}$$

$$r_3 = R_3[(1-r_0^2)(1-r_1^2)(1-r_2^2)]^{-1}$$

etc.

This is similar in form to the algorithm that is employed in B-mode ultrasound imaging, that is, without contributions from secondary and higher order reflections.

With use of the overtones (resonance frequencies higher than the fundamental) in the IREL method, it becomes possible to estimate the contributions from the secondary and higher order reflections. The resulting form of the reflection coefficients will hence be similar to those obtained by the GWA algorithm.

These frequency-based approaches are contemplated as an alternate means by which to achieve cavity area-profile reconstruction. Unlike pulse reflectometry, the IREL method does not require a wavetube, and is compact and miniaturizable. It usable with only a single microphone, and avoids the erratic instability seen with two-microphone reflectometers.

FIG. 10 shows a general flow diagram of an exemplary hybrid-frequency specific method as described above.

Figure 5:
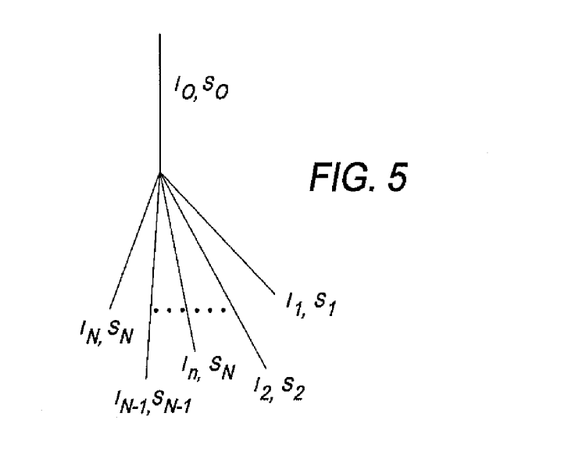
FIG. 5 shows a schematic diagram depicting a first-order bush like structure with a single node in accordance with the present invention.

The branching network of the pulmonary tree has multiple successive bifurcations. One way of viewing lung resonance phenomena is as a first-order bush like structure with a single node, consisting of a parent trunk of length $1_0$, and cross-sectional area $S_0$ dividing into N daughter branches of variable length $1_n$, and area $S_n$. Asymmetry of the branching network has been shown to lead to clumping of system values into distinct clusters in the low frequency range. Hence, the current frequency-specific approach can be interpreted as a means of quantitating the contribution to the power spectrum of the clumped eigenvalues that share a common acoustic equivalent length $1_N$, as shown in FIG. 5 above.

Additional measures to enhance the area ratio calculation include considerations of phase, signal inversion, and anti-resonance.

Modified Circle System for Embedded AR Device

In an exemplary embodiment in accordance with the present invention a modified circle system for embedded AR Device has been developed.

The most frequently used anesthesia breathing system in the USA is the circle system. The circle system is so named because its components are arranged in the form of a circle. The components are (1) $CO_2$ absorber/absorbent, (2) fresh gas inlet, (3) unidirectional inspiratory and expiratory valves, (4) pressure gauge, (5) a manual reservoir bag, and (6) a scavenging system connection.

Figure 6:
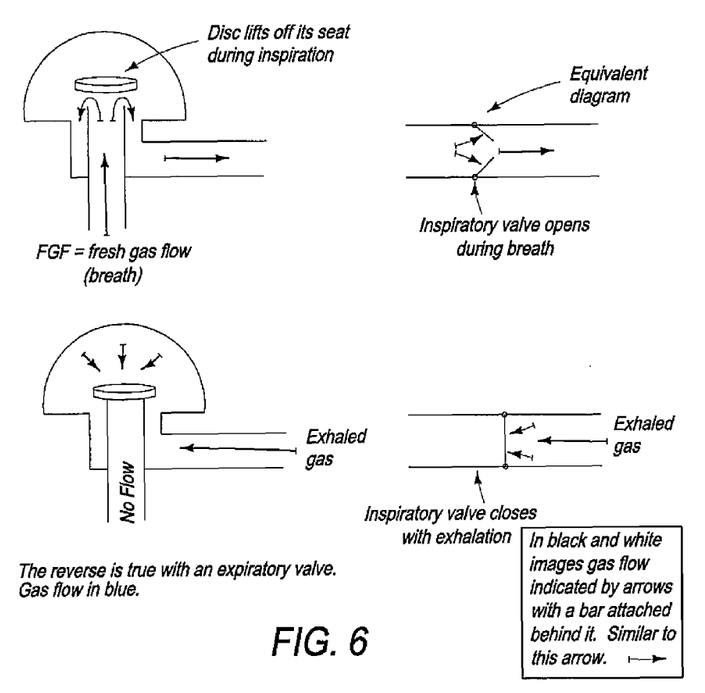
FIG. 6 shows a schematic diagram depicting the inspiratory valve of a circle system.

Two unidirectional valves are used in a circle system. The inspiratory valve directs the flow of gas to the patient, whereas the expiratory valve directs the flow of gas away from the patient. For example, one type of unidirectional valve consists of a thin disc covered with a clear dome that allows visual inspection of the valve. Gas enters at the bottom and flows through it, raising the valve. Reversing the gas flow will cause the disc to contact the seat, stopping further retrograde flow. An example of an inspiration valve is depicted in FIG. 6.

Figure 7:
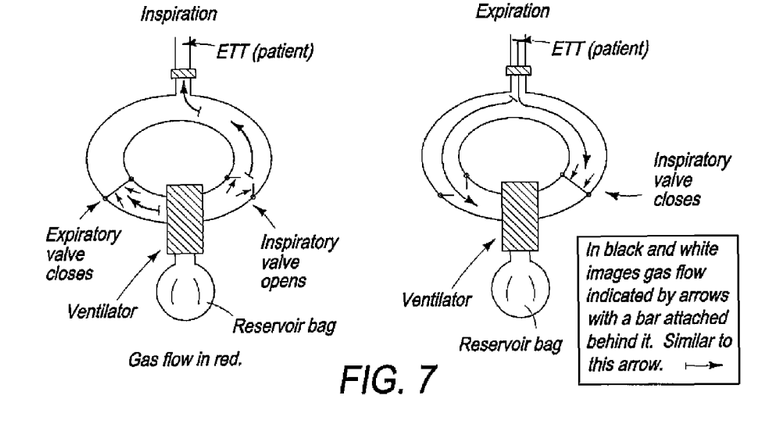
FIG. 7 shows a schematic diagram depicting the operation of a circle system.

FIG. 7 depicts the normal operation of the circle system, illustrating how the circle system works when used with a mechanical ventilator. During a mechanical breath, the delivered tidal volume (breath) goes down both the inspiratory and the expiratory limbs.

During Inspiration: When the breath is given, the inspiratory valve ovens. When the breath is given, the expiratory valve closes. Gas can go only one way, i.e., toward the patient.

During expiration: Expiration is passive, due to recoil of the previously expanded lung and chest wall. When the patient exhales, the expiratory valve opens. When the patient exhales, the inspiratory valve closes. Gas can only go one way, i.e., away from the patient. Part of the exhaled gas is recycled in the circle system, and part of it may exit into the scavenging system.

During End-Expiration: In between inspiration and expiration, there is a pause, the end-expiration period. During this period the inspiratory and expiratory valves are completely closed. This is the optimal time to obtain an acoustic reflectometry (AR) measurement.

Figure 8:
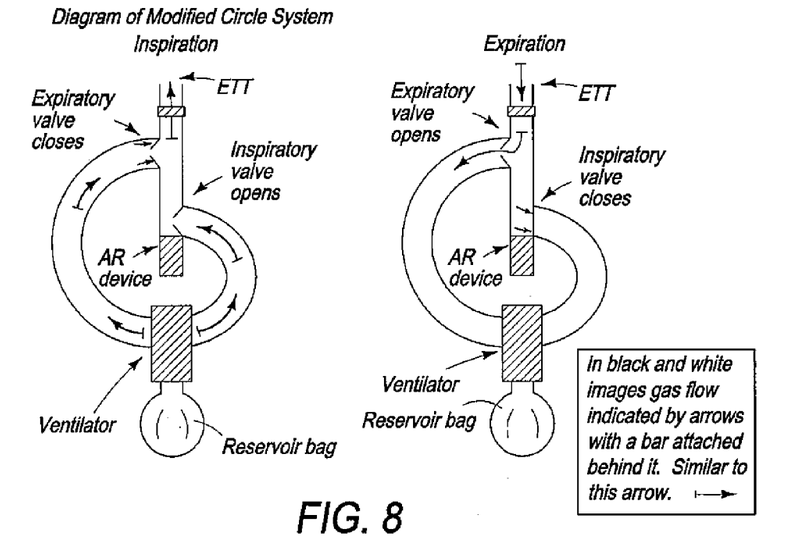
FIG. 8 shows a schematic diagram depicting a modified circle system in accordance with the present invention.
Figure 9:
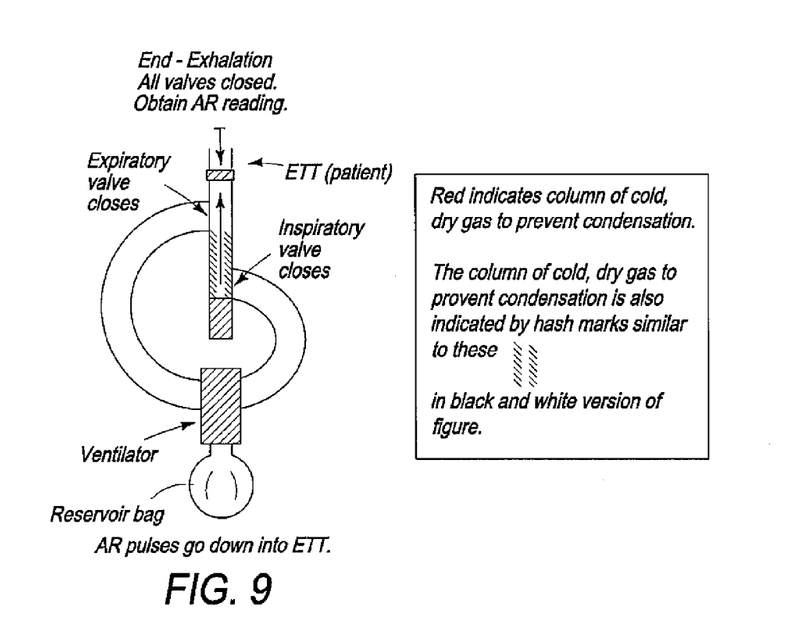
FIG. 9 shows a schematic diagram of the modified circle system depicted in FIG. 8, during end-exhalation.

Condensation when an AR device is attached to a circle system is a problem. In an exemplary embodiment in accordance with the present invention, the circle system has been modified to solve this problem among others. The circle system is modified as follows in accordance with the present invention an exemplary embodiment of which is depicted in FIGS. 8 and 9:

(I) Create a special port to connect to the AR device.

(2) Place the expiratory valve closer to the endotracheal tube (ETT) adaptor. In this manner, when the patient exhales and leaves the ETT, the exhaled gas leaves immediately through the nearby expiratory valve.

(3) The inspiratory valve is placed farther away from the ETT adaptor. Indeed, the inspiratory valve is placed close to the end of the AR wavetube. The placement of the valves, as described in (1) and (2), creates a space between the inspiratory and the expiratory valve (say, about 4 cm) that has a column of cold, dry gas. This prevents exhaled gas with water vapor from entering and condensing on the AR device.

At end-exhalation, when no mechanical breath is given and no passive exhalation occurs, the inspiratory and expiratory valves are effectively closed. This is the best time to obtain an AR measurement with any activated AR device, with or without a wavetube.

In the above exemplary embodiment the standard circle system has been modified such that the inspiratory and expiratory limbs of the breathing circuit, and their associated valves, are placed in non-standard locations. A port has been created for the attachment of the acoustic reflectometer (AR).

In another exemplary embodiment in accordance with the present invention it is also possible to design the AR device so that, in addition to a port for its own attachment, it has two additional built-in ready-made connecting ports to the inspiratory and expiratory limbs. In this manner, the device can be readily integrated into any standard circle system.

Another exemplary embodiment is to create a hole within the loudspeaker. Such a hole allows continuous entry of cold dry gas (e.g., air) into the region in front of the loudspeaker and prevents condensation on the resonance device.

Exemplary embodiments of the present invention can be used, for example, to monitor an endotracheal tube to notify an appropriate person that fluid or some other foreign matter is partially or totally obstructing the lumen of the tube. Then corrective action can be taken by the notified person if necessary.

Exemplary embodiments of the present invention can be modified by one of ordinary skill in the art to be operable on humans or animals or any system where measurements of a cavity are necessary.

In another aspect, the present invention also provides a method for modifying a breathing circuit, which incorporates an acoustic resonance-based device according to embodiments of the present invention, in such a way that a measurement can be obtained at end-exhalation when the inspiratory and expiratory valves are both closed. This is the optimal time for such a measurement within a mechanical ventilation system that is connected to a breathing circuit with moving valves. This technique prevents sound leakage through the valves, and allows a direct straight line measurement from the resonance device to the interior of a cavity.

Embodiments of the present invention include its incorporation within a breathing circuit such that no detachment of the breathing tube is required, and such embodiments are resistant to the effects of breathing circuit humidification, pressure and temperature variations.

It should also be understood that the above description is only representative of illustrative embodiments. For the convenience of the reader, the above description has focused on a representative sample of possible embodiments, that are illustrative of the principles of the invention, and has not attempted to exhaustively enumerate all possible variations. That alternative embodiments may not have been presented for a specific portion of the invention is not to be considered a disclaimer of those alternate embodiments. Other applications and embodiments can be straightforwardly implemented without departing from the spirit and scope of the present invention. It is therefore intended, that the invention not be limited to the specifically described embodiments, but the invention is to be defined in accordance with that claims that follow, It can be appreciated that many of those undescribed embodiments are within the literal scope of the following claims, and that others are equivalent.

What is claimed is:

1. A resonance-based acoustic reflectometer for determining a cross-sectional area-distance profile of a tubular cavity, said cavity having a distal end and a proximal end, said reflectometer comprising:

a sound generator for generating probing sound waves to be projected into the cavity from the proximal end;

a sound receiver for receiving sound waves from the cavity at the proximal end of the cavity; and a processor configured for determining the cross-sectional area-distance profile of the cavity based on resonance frequencies associated with standing waves resulting from constructive interferences between the probing sound wave and sound waves reflected from the cavity's inner structures.

2. The reflectometer of claim 1, wherein the processor is configured to determine the cross-sectional area-distance profile of the cavity by performing the steps of:

analyzing sounds received by the sound receiver to identify resonance frequencies associated with distances within the tubular cavity: and computing cross-sectional areas at each distance iteratively starting from the distance most proximal to the proximal end of the cavity to the distance most distal to the proximal end of the cavity, wherein computation of a cross-sectional area at a distance is based on the resonance frequency associated with the distance and the cross-sectional area of the preceding distance.

3. The reflectometer of claim 1, further comprising an attenuator for silencing unwanted reflections.

4. The reflectometer of claim 1, wherein the reflectometer is miniaturized and adapted for use with an endotracheal tube so as to detect the endotracheal tube's placement in a subject's airway cavity.

5. A resonance-based acoustic reflectometry method for determining a cross-sectional area-distance profile of a tubular cavity, said tubular cavity having a proximal end and a distal end, said method comprising:
   a. providing probing sound waves using a sound generator;
   b. projecting the probing sound waves into the cavity to be reflected by the cavity's inner structures and allowing the probing sound waves to interact with the reflected sounds so as to create resonances;
   c. analyzing the sound waves to identify resonance frequencies and associating the resonance frequencies with axial distances of the cavity; and
   d. computing the cross-sectional areas iteratively at each axial distance starting from the proximal end to the distal end of the cavity, wherein computation of cross-sectional area at an axial distance is based on the resonance frequency associated with the axial distance and the cross-sectional area at the preceding axial distance.

6. The method of claim 5, wherein said probing sound waves are selected from the group consisting of white noise, fixed wavelength sound waves, continuous sinusoidal sound waves, single frequency sound wave having a frequency that is a multiple of the fundamental frequency, or a multiple frequency sound wave having a predetermined range of frequencies.

7. The method of claim 5, wherein the tubular cavity is a non-bifurcated cavity.

8. The method of claim 5, wherein the tubular cavity is a multiply bifurcated cavity.

9. The method of claim 5, wherein analysis of the sound waves is done in a time-gated manner.

10. The method of claim 5, further comprising the step of:
    projecting a white noise sound into the cavity and detecting a lowest resonance frequency, and
    determining an overall length of the tubular cavity based on said lowest resonance frequency.

11. A resonance-based acoustic reflectometer for determining an area-distance profile of a tubular cavity, said tubular cavity having a proximal end and a distal end, said reflectometer comprising:
    a sound generator for generating a-probing sound waves to be projected into the tubular cavity from the proximal end and reflected by the cavity's internal structures;
    a processor configured to perform the steps of:
        analyzing the reflected sounds to identify resonance frequencies and associating each resonance frequency with a distance within the cavity; and
        computing cross-sectional areas at each distance within the cavity starting from the proximal end to the distal end of the cavity based on the resonance frequency associated with the distance.

12. A resonance-based acoustic reflectometer, comprising:
    a sound generator for generating a probing sound for delivery through a body cavity;
    a sound receiver for receiving sound waves returning from within the body cavity, said returning sound is formed by allowing the probing sound to interfere with sounds reflected from within the body cavity; and
    a processor in communication with said sound receiver for transforming the returning sound into a cross-sectional area-distance profile of the body cavity,
    wherein the processor is configured to transform the returning sound into the cross-sectional area-distance profile by performing a resonance-based method comprising the steps of:
    analyzing the returning sound to determine resonance frequencies associated with a plurality of predetermined distances within the body cavity; and
    determining a cross-sectional area for each distance iteratively starting from the distance most proximal to the opening of the body cavity based on:
        the resonance frequency associated with the distance, and
        a ratio between the cross-sectional area of the distance and the cross-sectional area of the distance in the preceding iteration,
    wherein in the first iteration, the ratio is between the cross-sectional area of the distance most proximal to the cavity opening and the cross-sectional area of the cavity opening.

\* \* \* \* \*